US008674072B2

(12) United States Patent
Dal Farra et al.

(10) Patent No.: US 8,674,072 B2
(45) Date of Patent: *Mar. 18, 2014

(54) COSMETIC AND/OR PHARMACEUTICAL COMPOSITION COMPRISING A PEPTIDIC HYDROLYZATE THAT CAN REINFORCE THE BARRIER FUNCTION

(75) Inventors: Claude Dal Farra, Kerthonkson, NY (US); Nouha Domloge, Valbonne (FR); Jean-Marie Botto, Valbonne (FR)

(73) Assignee: ISP Investments Inc., Wilmington, DE (US)

( * ) Notice: Subject to any disclaimer, the term of this patent is extended or adjusted under 35 U.S.C. 154(b) by 81 days.

This patent is subject to a terminal disclaimer.

(21) Appl. No.: 13/264,035

(22) PCT Filed: Apr. 15, 2010

(86) PCT No.: PCT/FR2010/000311
§ 371 (c)(1),
(2), (4) Date: Oct. 12, 2011

(87) PCT Pub. No.: WO2010/119191
PCT Pub. Date: Oct. 21, 2010

(65) Prior Publication Data
US 2012/0094920 A1 Apr. 19, 2012

(30) Foreign Application Priority Data
Apr. 15, 2009 (FR) ..................... 09 01822

(51) Int. Cl.
*C07K 5/10* (2006.01)
*C07K 7/06* (2006.01)
*C07K 4/10* (2006.01)
*C07K 4/06* (2006.01)
*A61Q 17/00* (2006.01)
*A61Q 17/04* (2006.01)
*A61Q 19/08* (2006.01)
*A61K 38/07* (2006.01)
*A61K 38/08* (2006.01)
*A61K 8/64* (2006.01)
*A61K 8/97* (2006.01)
*C07K 5/103* (2006.01)
*A61Q 19/00* (2006.01)
*A61K 38/01* (2006.01)

(52) U.S. Cl.
CPC ... *C07K 5/10* (2013.01); *C07K 7/06* (2013.01); *C07K 5/1008* (2013.01); *C07K 4/10* (2013.01); *C07K 4/06* (2013.01); *A61Q 17/00* (2013.01); *A61Q 17/04* (2013.01); *A61Q 19/004* (2013.01); *A61Q 19/005* (2013.01); *A61Q 19/08* (2013.01); *A61K 38/07* (2013.01); *A61K 38/08* (2013.01); *A61K 38/011* (2013.01); *A61K 8/64* (2013.01); *A61K 8/97* (2013.01)
USPC .......... 530/329; 530/300; 530/330; 514/18.6; 514/18.8

(58) Field of Classification Search
CPC .......... C07K 5/10; C07K 7/06; C07K 5/1008; C07K 4/10; C07K 4/06; A61Q 17/00; A61Q 17/04; A61Q 19/004; A61Q 19/005; A61Q 19/08; A61K 38/07; A61K 38/011; A61K 8/64; A61K 8/97
USPC ................. 530/300, 329, 330; 514/18.6, 18.8
See application file for complete search history.

(56) References Cited

U.S. PATENT DOCUMENTS

| | | | |
|---|---|---|---|
| 4,139,619 A | 2/1979 | Chidsey, III | |
| 4,596,812 A | 6/1986 | Chidsey, III et al. | |
| 5,733,558 A | 3/1998 | Breton et al. | |
| 5,977,082 A | 11/1999 | Gatti et al. | |
| 7,431,919 B2 | 10/2008 | Travkina et al. | |
| 7,887,858 B2 | 2/2011 | Cauchard et al. | |
| 8,394,390 B2 * | 3/2013 | Galeotti et al. | 424/250.1 |
| 2004/0141939 A1 | 7/2004 | Dal Farra et al. | |
| 2005/0272097 A1 | 12/2005 | Calenoff | |
| 2007/0274937 A1 | 11/2007 | Dal Farra et al. | |
| 2008/0268077 A1 | 10/2008 | Vielhaber | |
| 2009/0016971 A1 | 1/2009 | Gaudry et al. | |
| 2010/0003344 A1 | 1/2010 | Cassin | |

FOREIGN PATENT DOCUMENTS

| | | |
|---|---|---|
| EP | 0265099 | 4/1988 |
| EP | 0327263 | 8/1989 |
| EP | 0695801 | 2/1996 |
| EP | 0738510 | 10/1996 |
| EP | 0902035 | 3/1999 |
| EP | 1152062 | 11/2001 |
| EP | 1281401 | 2/2003 |
| EP | 1272148 | 6/2006 |
| EP | 1707189 | 10/2006 |
| FR | 2789312 | 8/2000 |

(Continued)

OTHER PUBLICATIONS

Dal Farra et al, machine translation of FR 2915384, pp. 1-18. Apr. 27, 2007.*
Dal Farra et al, machine translation of FR 2904552, pp. 1-16. Aug. 3, 2006.*
SEQ ID No. 30601 from US Patent No. 8394390. Mar. 2013.*
Effects of Aging on the Skin, from Merck manual, p. 1. Accessed Apr. 9, 2012.*
Chronic effects of Sunlight from Merck manual, pp. 1-2. Accessed Aug. 23, 2012.*
"Designing Custom Peptides," from SIGMA Genosys, http://www.sigma-genosys.com/peptide_design.asp, pp. 1-2, (accessed Dec. 16, 2004).
Berendsen, H.J.C., "A Glimpse of the Holy Grail?" Science, 1998, 282: 642-643.

(Continued)

*Primary Examiner* — Julie Ha
(74) *Attorney, Agent, or Firm* — Thompson Hine L.L.P.

(57) ABSTRACT

A peptidic hydrolyzate enriched in bioactive peptide, capable of reinforcing the skin barrier function and stimulating epidermal differentiation is described. Additionally, a cosmetic and/or pharmaceutical composition that includes a physiologically acceptable medium and the peptidic hydrolyzate as active principle are described. The cosmetic composition activates the HMG-CoA reductase in the cutaneous cells and treats the cutaneous signs of aging and photo-aging.

18 Claims, 3 Drawing Sheets

(56) References Cited

FOREIGN PATENT DOCUMENTS

| | | |
|---|---|---|
| FR | 2868309 | 10/2005 |
| FR | 2887772 | 1/2007 |
| FR | 2904552 | 2/2008 |
| FR | 2911779 | 8/2008 |
| FR | 2915384 | 10/2008 |
| FR | 2925325 | 6/2009 |
| FR | 2925326 | 6/2009 |
| FR | 2925327 | 6/2009 |
| FR | 2925330 | 6/2009 |
| FR | 2927254 | 8/2009 |
| JP | 07-316023 | 12/1995 |
| WO | 03/008438 | 1/2003 |
| WO | 03/023067 | 3/2003 |
| WO | 03/068184 | 8/2003 |
| WO | 03/087831 | 10/2003 |
| WO | 2004/031211 | 4/2004 |
| WO | 2004/058282 | 7/2004 |
| WO | 2004/096168 | 11/2004 |
| WO | 2005/047328 | 5/2005 |
| WO | 2005/080985 | 9/2005 |
| WO | 2005/107697 | 11/2005 |
| WO | 2005/111081 | 11/2005 |
| WO | 2008/015343 | 2/2008 |

OTHER PUBLICATIONS

Bradley, C.M. et al., "Limits of Cooperativity in a Structurally Modular Protein: Response of the Notch Ankyrin Domain to Analogous Alanine Substitutions in Each Repeat," J. Mol. Biol., 2002, 324: 373-386.

Definition of "derivative" from http://cancerweb.ncl.ac.uk/omd/about.html, pp. 1-5 (accessed Jul. 7, 2005).

Ngo, J.T. et al., "Computational Complexity Protein Structure Prediction, and the Levinthal Paradox, The Protein Folding Problem and Tertiary Structure Predictio," K. Merc Jr. and S. Le Grand Edition, 1994, pp. 491-495.

Rudinger, J., "Characteristics of the amino acids as components of a peptide hormone sequence," Peptide Hormones, J.A. Parsons Edition, University Party Press, Jun. 1976, pp. 1-7.

Schinzel, R. et al., "The phosphate recognition site of *Escherichia coli* maltodextrin phosphorylase," FEBS, Jul. 1991, 286(1,2): 125-128.

Voet, D. et al., Biochemistry, Second Edition, John Wiley & Sons, Inc., 1995, pp. 235-241.

PCT, International Search Report, International Application No. PCT/FR2010/000311 (mailed Jul. 6, 2010; published Oct. 21, 2010).

Ghadially, R. et al., "The Aged Epidermal Permeability Barrier," *The Journal of Clinical Investigations, Inc.*, vol. 95, pp. 2281-2290 (May 1995).

Luskey, K.L. et al., "Human 3-Hydroxy-3-methylglutaryl Coenzyme A Reductase," *The Journal of biological Chemistry*, vol. 260, No. 18, pp. 10271-10277 (Aug. 25, 1985).

Martini, M.C., "Biochemical Analysis of epidermal lipids," *Pathologie Biologie*, 51, pp. 267-270 (2003).

Menon, G.K. et al., "De novo sterologenesis in the skin. II. Regulation by cutaneous barrier requirements," *Journal of Lipid Research*, vol. 26, pp. 418-427 (1985).

Norlén, L. et al., "Inter- and Intra-Individual Differences in Human Stratum Corneum Lipid Content Related to Physical Parameters of Skin Barrier Function In Vivo," *J. Invest. Dermatol.*, 112 (1), pp. 72-77 (1999).

Proksch, E. et al., "Barrier function regulates epidermal lipid and DNA synthesis," *British Journal of Dermatology*, 128, pp. 473-482 (1993).

Gourley, D.G., et al., "HMG-CoA Reductase: a Novel Target for Antimicrobial Chemotherapy," Abstracts of the Interscience Conference on Antimicrobial Agents and Chemotherapy, vol. 43, 2003, p. 219, XP035587 & 43rd Annual Interscience Conference on Antimicrobial Agents and Chemotherapy, Chicago, IL, USA, Sep. 14-17, 2003 (abstract).

Kullmann, W., "Proteases as Catalysts for Enzymic Syntheses of Opioid Peptides," The Journal of Biological Chemistry, vol. 255, No. 17, pp. 8234-8238 (Sep. 10, 1980).

Office Action, U.S. Appl. No. 13/505,348 (Sep. 12, 2012).

Office Action, U.S. Appl. No. 13/505,348 (Apr. 9, 2013).

International Search Report, International Application No. PCT/FR2010/000724 (Mar. 3, 2011).

International Preliminary Report on Patentability, International Application No. PCT/FR2010/000724 (Jun. 5, 2012).

Birch, M.P. et al., "Hair density, hair diameter and the prevalence of female pattern hair loss," British Journal of Dermatology, 144, pp. 297-304 (2001).

Courtois, M. et al., "Ageing and hair cycles," British Journal of Dermatology, 132, pp. 86-93 (1995).

Langbein, L. et al., "The Catalog of Human Hair Keratins," The Journal of Biological Chemistry, vol. 276, No. 37, pp. 35123-35132 (Sep. 14, 2001).

Lenoir, M.-C. et al., "Outer Root Sheath Cells of Human Hair Follicle Are Able to Regenerate a Fully Differentiated Epidermis in Vitro," Developmental Biology, vol. 130, pp. 610-620 (1988).

Pelfini, C. et al., "Cheveux et vieillissement," J. Méd. Esth. et Chir. Derm., vol. XIV, No. 53, pp. 9-14 (Mar. 1987).

Porter, R.M. et al., "Keratin K6irs is specific to the inner root sheath of hair follicles in mice and humans," British Journal of Dermatology, 145, pp. 558-568 (2001).

Alopecia from Merck Manual, pp. 1-5 (accessed Jul. 2, 2013).

\* cited by examiner

Figure 1 HPLC chromatogram of a einkorn hydrolyzate
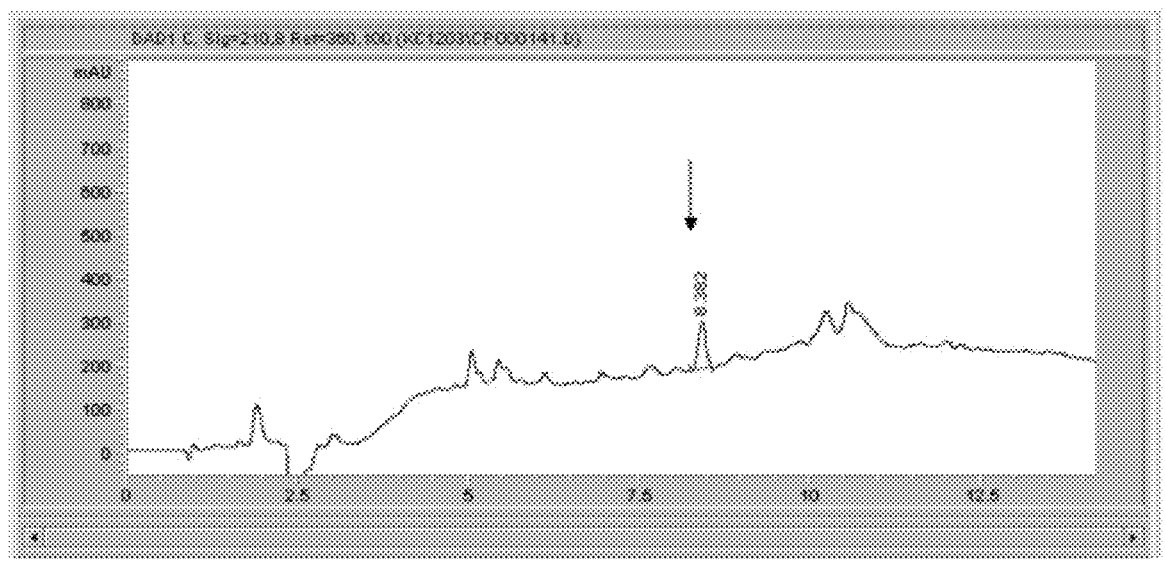
Figure 2 HPLC chromatogram of a potato hydrolyzate
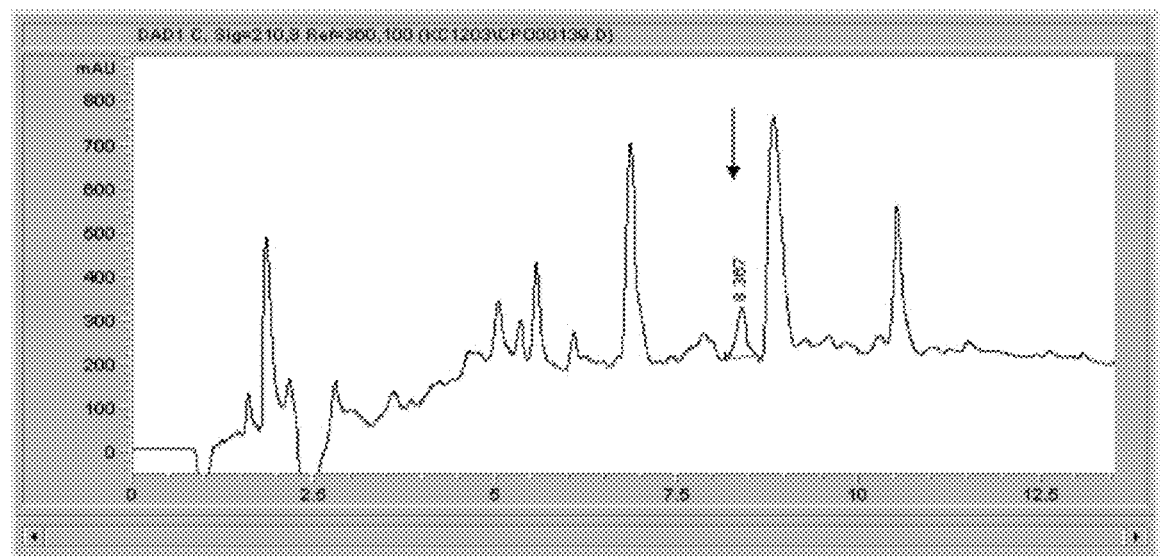

Figure 3 HPLC chromatogram of a corn hydrolyzate
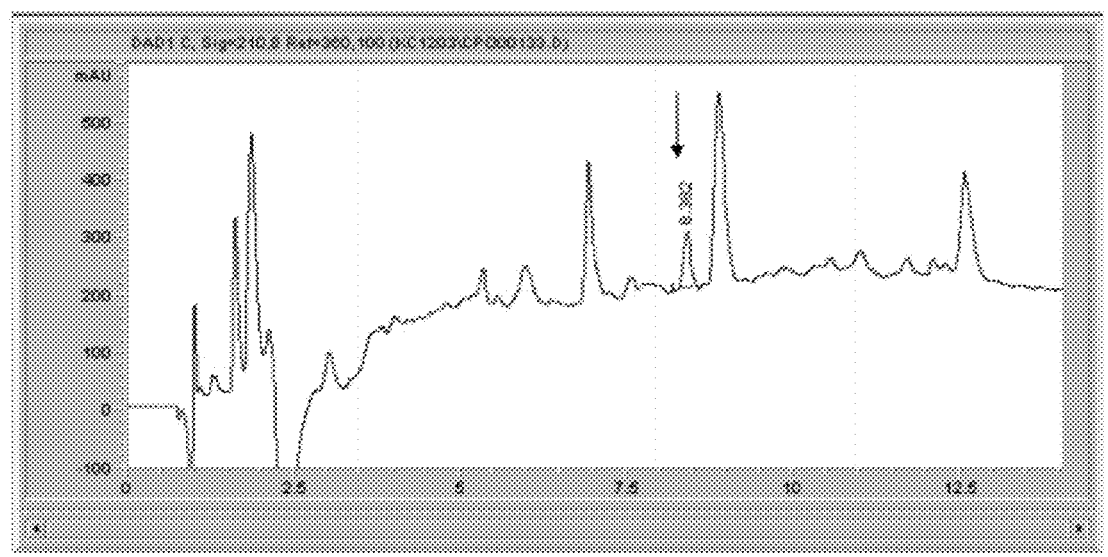
Figure 4 HPLC chromatogram of a pea hydrolyzate
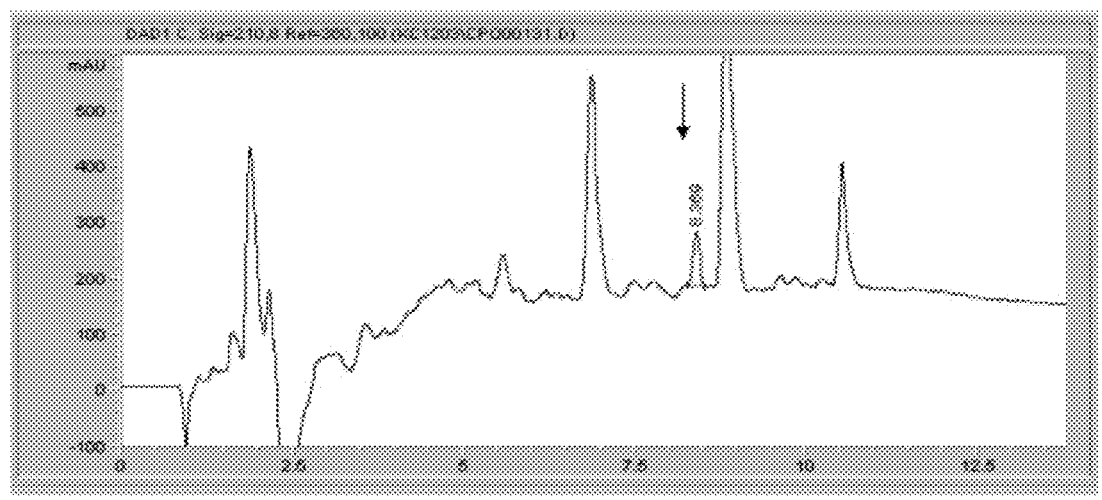

Figure 5 HPLC chromatogram of a soy hydrolyzate
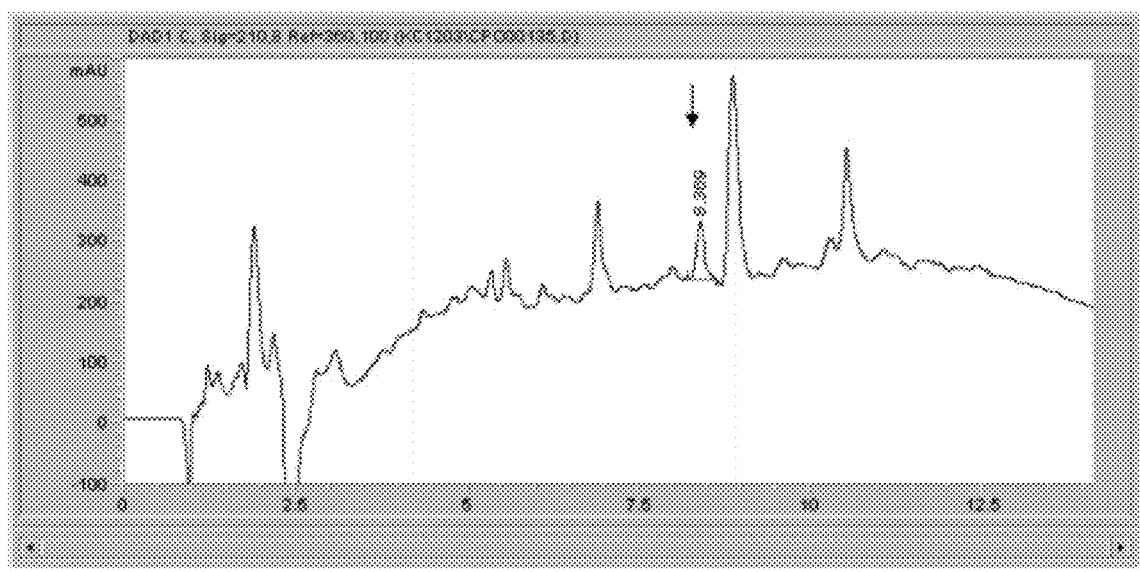
Figure 6 HPLC chromatogram of a Saccharomyces hydrolyzate
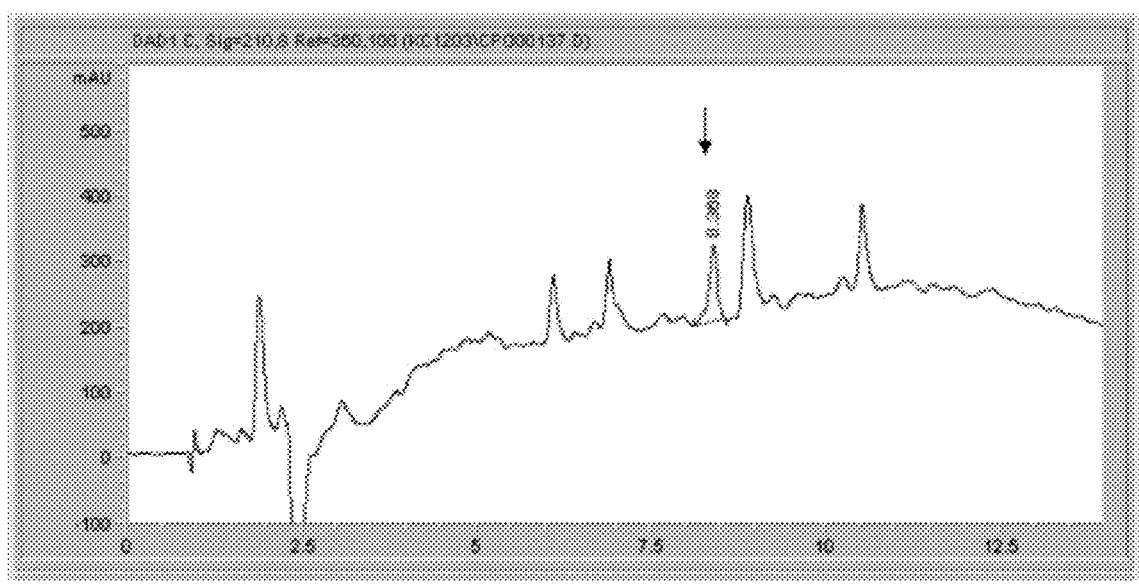

SEQUENCE LISTING

<160> NUMBER OF SEQ ID NOS: 8

<210> SEQ ID NO 1
<211> LENGTH: 6
<212> TYPE: PRT
<213> ORGANISM: Saccharomyces cerevisiae
<220> FEATURE:
<221> NAME/KEY: MISC_FEATURE
<223> OTHER INFORMATION: The sequence also may be obtained from Triticum
      monococcum, Solanum tuberosum, Zea mays L, Pisum sativum L, or
      Glycine Max L.

<400> SEQUENCE: 1

Ala Glu Gly Leu Ser Ile
1               5

<210> SEQ ID NO 2
<211> LENGTH: 5
<212> TYPE: PRT
<213> ORGANISM: Saccharomyces cerevisiae
<220> FEATURE:
<221> NAME/KEY: MISC_FEATURE
<223> OTHER INFORMATION: The sequence also may be obtained from Triticum
      monococcum, Solanum tuberosum, Zea mays L, Pisum sativum L, or
      Glycine Max L.

<400> SEQUENCE: 2

Leu Gly Glu Ser Leu
1               5

<210> SEQ ID NO 3
<211> LENGTH: 5
<212> TYPE: PRT
<213> ORGANISM: Saccharomyces cerevisiae
<220> FEATURE:
<221> NAME/KEY: MISC_FEATURE
<223> OTHER INFORMATION: The sequence also may be obtained from Triticum
      monococcum, Solanum tuberosum, Zea mays L, Pisum sativum L, or
      Glycine Max L.

<400> SEQUENCE: 3

Val Gly Glu Leu Thr
1               5

<210> SEQ ID NO 4
<211> LENGTH: 5
<212> TYPE: PRT
<213> ORGANISM: Saccharomyces cerevisiae
<220> FEATURE:
<221> NAME/KEY: MISC_FEATURE
<223> OTHER INFORMATION: The sequence also may be obtained from Triticum
      monococcum, Solanum tuberosum, Zea mays L, Pisum sativum L, or
      Glycine Max L.

<400> SEQUENCE: 4

Ile Gly Glu Leu Ser
1               5

<210> SEQ ID NO 5
<211> LENGTH: 5
<212> TYPE: PRT
<213> ORGANISM: Saccharomyces cerevisiae
<220> FEATURE:
<221> NAME/KEY: MISC_FEATURE
<223> OTHER INFORMATION: The sequence also may be obtained from Triticum
      monococcum, Solanum tuberosum, Zea mays L, Pisum sativum L, or
      Glycine Max L.

<400> SEQUENCE: 5

```
Ala Gly Glu Leu Ser
1               5

<210> SEQ ID NO 6
<211> LENGTH: 5
<212> TYPE: PRT
<213> ORGANISM: Saccharomyces cerevisiae
<220> FEATURE:
<221> NAME/KEY: MISC_FEATURE
<223> OTHER INFORMATION: The sequence also may be obtained from Triticum
      monococcum, Solanum tuberosum, Zea mays L, Pisum sativum L, or
      Glycine Max L.

<400> SEQUENCE: 6

Gly Glu Leu Thr Ile
1               5

<210> SEQ ID NO 7
<211> LENGTH: 4
<212> TYPE: PRT
<213> ORGANISM: Saccharomyces cerevisiae
<220> FEATURE:
<221> NAME/KEY: MISC_FEATURE
<223> OTHER INFORMATION: The sequence also may be obtained from Triticum
      monococcum, Solanum tuberosum, Zea mays L, Pisum sativum L, or
      Glycine Max L.

<400> SEQUENCE: 7

Gly Glu Leu Ser
1

<210> SEQ ID NO 8
<211> LENGTH: 6
<212> TYPE: PRT
<213> ORGANISM: Artificial Sequence
<220> FEATURE:
<223> OTHER INFORMATION: synthetic peptide

<400> SEQUENCE: 8

Gly Pro Gln Gly Pro Gln
1               5
```

COSMETIC AND/OR PHARMACEUTICAL COMPOSITION COMPRISING A PEPTIDIC HYDROLYZATE THAT CAN REINFORCE THE BARRIER FUNCTION

The present invention is situated in the cosmetic and pharmaceutical field, and more particularly in the dermatology field. The invention relates to a peptidic hydrolyzate enriched in bioactive peptide, capable of reinforcing the skin barrier function and stimulating epidermal differentiation. The bioactive peptide is characterized in that it comprises from 4 to 6 amino acids including at least one glycine residue, one leucine residue and one glutamic acid residue. Preferably, the active principle comes from the hydrolysis of plant proteins chosen from among einkorn, potato, corn, pea, soy or yeast proteins from the *Saccharomyces* genus. The invention also relates to a composition comprising, in a physiologically acceptable medium, a peptidic hydrolyzate enriched in bioactive peptide as the active principle capable of reinforcing the barrier function of the epidermis. The invention also relates to a pharmaceutical composition comprising this novel active principle as a drug. Lastly, the invention relates to the use of said peptidic hydrolyzate as an active principle to activate HMG-CoA reductase. The invention further relates to the use of said peptidic hydrolyzate as an active principle to reinforce the skin barrier function and stimulate epidermal differentiation. The invention further applies to a cosmetic treatment method intended to prevent and/or combat the external stresses and signs of cutaneous aging.

The first function of the epidermis is to constitute a barrier between the external environment and the internal environment. The outermost layer of the epidermis, the horny layer of the epidermis or *stratum corneum*, ensures this function. It is composed of keratinocytes in the last stage of their differentiation, corneocytes, sealed to each other by thick intercellular cement that is both flexible and impermeable. Therefore, a cellular compartment constituted of corneocytes and an extracellular compartment mainly constituted of lipids, organized into multilamellar structures, are distinguished in the *stratum corneum*.

The lipid content of the human *stratum corneum* is estimated at 15% of cholesterol ester, 16% of free long-chain saturated fatty acids, 32% of cholesterol and 37% of ceramides, although inter-individual variations are rather significant (Norlen L. et al. J. Invest. Dermatol. 1999; 112(1) p. 72-77). These lipids are synthesized by keratinocytes from intermediate layers of the epidermis, and secreted in specialized organites called "lamellar bodies" or Odland bodies. In particular, the epidermis is a very active site for synthesizing cholesterol. The rate-limiting step of this synthesis, and the most finely regulated step, is the conversion of 3-hydroxy-3-methylglutaryl-Coenzyme A (HMG-CoA) into mevalonate. This step is catalyzed by a membrane-bound enzyme called HMG-CoA-reductase (E.C. 1.1.1.34). Human genome sequencing data show that at least 2 isoforms for HMG-CoA reductase exist, coded by a unique gene, located on chromosome 5 (Luskey et al., J Biol Chem., 1985 260(18), p. 10271-7).

In the skin, cholesterol plays a role in the fluidity of the membranes and, in particular, it seems to ensure the mobility of hydrocarbon chains in lipid bilayers (Martini M. C., Pathol. Biol. 2003, (51), p. 267-270). Thus, in physiological situations, cholesterol is synthesized at a level necessary for maintaining homeostasis. On the other hand, following a sudden alteration in the cutaneous barrier, a significant and rapid increase in the synthesis of cholesterol is observed, associated with an increase in the expression and activity of HMG-CoA reductase (Menon G. K. et al., J. Lipid, Res., 1985, (26), P. 418-427).

The key role of HMG-CoA reductase makes it a prime target for modulating the expression of cholesterol in the organism. Therefore, a class of pharmacological compounds called statins, intended to inhibit HMG-CoA reductase, has been developed with the goal of lowering circulating cholesterol. This inhibitor effect of statins is also manifested in human skin. In fact, the experimental administration of statins by topical route disrupts the barrier function of the skin (Proksch E. et al., British J. Dermatol., 1993, (128), p. 473-482). These results confirm the importance of cholesterol in the epidermal barrier function and the central role of HMG-CoA reductase in modulating its synthesis.

When skin ages, the integrity of the skin barrier, as well as its capacities for repair, change. A global deficiency in lipids is observed, resulting in a reduction of lipid multilayers of the extracellular compartment of the stratum corneum. These functional changes correlate with an increased susceptibility of aged skins to external stresses (Ghadially R. et al., J Clin Invest., 1995 (95 (5), p. 2281-90).

Independently from intrinsic or photo-induced aging, alterations in the skin barrier may be produced during external stresses.

In this context, trying to prevent the alteration or reestablish the barrier function of the epidermis is desirable. In this particular domain, the direct supply of lipid substitutes, such as ceramides (EP 1 272 148, US2007/576937) or some cholesterol derivatives (FR 2 789 312) has largely been described. On the other hand, the use of vegetable oils to activate the synthesis of cutaneous lipids has also been described. (EP 1 707 189). In the cosmetics field, the molecular targeting of HMG-CoA reductase has already been exploited although in the goal of inhibiting this key enzyme, for example by using statins, already known for their HMG-COA-inhibiting properties, in the goal of obtaining an anti-aging effect (EP 0 738 510). However, to date, no document describes or suggests the object of the invention; i.e., a peptidic hydrolyzate enriched in bioactive peptide according to the invention may have properties of interest to reinforce the skin barrier function and stimulate epidermal differentiation. By this action, it is also possible to improve some pathological dysfunctions connected to the barrier function (hypersensitive, irritated or reactive skin, atopic eczema).

The first object of the present invention is a peptidic hydrolyzate enriched in bioactive peptide capable of reinforcing the barrier function of the epidermis, characterized in that the hydrolyzate comprises 4 to 6 amino acids including at least one glycine residue, one leucine residue and one glutamic acid residue.

In fact, the inventors have demonstrated a cosmetic and therapeutic, and particularly a dermatological, activity of peptidic hydrolyzates containing some particular peptides, called bioactive peptides hereafter.

In particular, it has been demonstrated that the peptidic hydrolyzate, enriched in bioactive peptide, when it is applied to the skin, reinforces the barrier function of the epidermis and stimulates epidermal differentiation. These properties have been demonstrated by better protection of the skin tissue in relation to external stresses and by an increase in the production of lipids constituting the horny layer of the epidermis.

According to the invention, "bioactive peptide" is understood to be a linkage of at least four amino acids, interlinked by peptide linkages or by modified peptide linkages and that have an in vivo or in vitro activity characteristic of the activity of the active principle according to the invention.

The characteristic biological activity according to the invention is defined in vitro by the capacity of the peptide to activate HMG-CoA reductase, either by increasing the protein synthesis of HMG-CoA reductase (by direct or indirect modulation of HMG-CoA reductase gene expression), or by increasing the enzymatic activity of HMG-CoA reductase, or by other biological processes such as stabilizing the HMG-CoA reductase protein or else stabilizing messenger RNA transcripts.

Skin is understood to refer to all of the covering tissues constituting the skin and mucosa, including the epithelial appendages (hair, eyelashes, body hair, eyebrows).

"Peptidic hydrolyzate" is understood to refer to a mixture of compounds predominantly represented by peptides or oligopeptides. According to the invention, the terms "peptidic hydrolyzate" or "active principle" will be used equally.

"Peptidic nature compounds" is understood to refer to fragments of proteins, peptides and free amino acids present in the peptidic hydrolyzate according to the invention.

"Topical application" is understood to refer to the act of applying or spreading the active principle according to the invention, or a composition containing it, to or on the surface of the skin or mucous membrane. "Physiologically acceptable" is understood to mean that the peptidic hydrolyzate according to the invention, or a composition containing it, is appropriate for entering in contact with the skin or mucosa without causing toxicity or intolerance reactions.

According to a particularly advantageous method of embodiment of the invention, the bioactive peptide contained in the hydrolyzate has a sequence of general formula (I)

in which:
$X_1$ is alanine, valine, isoleucine or no amino acid,
$X_2$ is serine or threonine,
$X_3$ is leucine, isoleucine or no amino acid.

According to a particularly preferred method of embodiment of the invention, the bioactive peptide has the sequence:

```
                                        (SEQ ID No. 1)
Ala-Glu-Gly-Leu-Ser-Ile (SEQ ID No. 2)
Leu-Gly-Glu-Ser-Leu (SEQ ID No. 3)
Val-Gly-Glu-Leu-Thr (SEQ ID No. 4)
Ile-Gly-Glu-Leu-Ser (SEQ ID No. 5)
Ala-Gly-Glu-Leu-Ser (SEQ ID No. 6)
Gly-Glu-Leu-Thr-Ile (SEQ ID No. 7)
Gly-Glu-Leu-Ser
```

According to a particularly interesting embodiment, the biologically active peptide corresponds to the SEQ ID No. 5 sequence.

The active principle according to the invention may be obtained by extraction of proteins of plant or yeast origin, followed by a controlled hydrolysis that releases the peptidic nature compounds, among which bioactive peptides are found.

The use of peptidic hydrolyzates, particularly low molecular weight peptidic hydrolyzates, presents many advantages in cosmetics. In addition to generating peptidic nature compounds that did not preexist in the starting protein mixture, hydrolysis and purification enable more stable mixtures to be obtained, that are easy to standardize and that do not cause dermatological or cosmetic allergic reactions.

It is also possible to use some hydrolyzed extracts without purifying the peptidic nature compounds corresponding to the bioactive peptides according to the invention, but by ensuring the presence of said peptides by suitable analytical means.

Very many proteins found in plants and yeasts are likely to contain bioactive peptides within their structure. Controlled hydrolysis enables these particular compounds of peptidic nature to be released. It is possible, but not necessary to carry out the invention, to extract either the relevant proteins first and then hydrolyze them, or perform hydrolysis first on a crude extract and then purify the peptidic nature compounds.

According to a preferred embodiment, said active principle comes from the hydrolysis of plant proteins chosen from among einkorn, potato, corn, pea, soy or yeast proteins of the *Saccharomyces* species. Preferably, the plants used are not subjected to prior fermentation.

Thus, the invention may be carried out by using small einkorn seeds (*Triticum monococcum*), which is a very old diploid wheat containing a particularly high protein level (Vallega 1992).

The invention may also be carried out by using potato tubers of the *Solanum* genus and more particularly of the *Solanum tuberosum* species. The tuber does not belong to the root of the plant, but to its buried stem, from which thinner branches called rhizomes extend, at the end of which the tubers form.

The invention may also be carried out by using the seeds from one of many plants of the *Zea* genus and preferentially the *Zea mays* L species. According to the invention, the plant material used will be the seed and, preferentially, the hull of the seed was removed by a hulling step.

The invention may also be carried out by using one of many plants from the pea family (Fabaceae). According to the invention, plants from the pea species *Pisum sativum* L are used. The term pea also designates the seed, itself rich in proteins (25%). The invention may also be carried out by using Fabaceae seeds, of the *Glycine* genus (soy) or soybean cake, and preferentially the *Glycine Max* L. species. According to the invention, the plant material used will be the seed and, preferentially, the hull of the seed was removed by a hulling step.

The invention may also be carried out by using yeasts of the *Saccharomyces* genus; and preferentially of the *Saccharomyces cerevisiae* species.

Any extraction or purification method known to the person skilled in the art may be used in order to prepare the hydrolyzate according to the invention.

In a first step, the seeds, or a specific part of the plant (leaves, tubers, roots, etc.) are milled by using a plant mill. The powder thus obtained may subsequently be "de-fatted" by using a conventional organic solvent (such as for example an alcohol, hexane or acetone).

With yeasts, in a first step, the yeasts are cultured conventionally in a suitable medium for their development, preferably in the presence of lactose. The yeasts are harvested by centrifugation and then suspended in a buffer solution, preferentially a phosphate buffer. In a second step, the cells are burst by using a French press or by using a ball mill, the majority of insoluble membrane components being separated by centrifugation or filtration.

Then proteins are extracted according to the modified conventional method (Osborne, 1924); the plant ground material or yeast lyzate is suspended in an alkaline solution containing an adsorbent product of the insoluble polyvinylpolypyrrolidone (PVPP) type (0.01-20%). Indeed, it was observed that subsequent hydrolysis and purification operations were facilitated by this means. In particular, the concentration of phenolic type substances, interacting with proteins, is markedly reduced.

The soluble fraction, containing proteins, carbohydrates and possibly lipids, is collected after the centrifugation and filtration steps. This crude solution is then hydrolyzed under controlled conditions to generate soluble peptides. Hydrolysis is defined as being a chemical reaction involving cleavage of a molecule by water, this reaction may be done in neutral, acidic or basic medium. According to the invention, hydrolysis is carried out chemically and/or advantageously by proteolytic enzymes. The use of plant origin endoproteases (papain, bromelin, ficin) and microorganisms (*Aspergillus, Rhizopus, Bacillus*, etc.) may then be cited. The hydrolysis conditions are chosen to promote bioactive peptide enrichment.

For the same reasons as above, i.e., the elimination of polyphenolic substances, a quantity of polyvinylpolypyrrolidone is added to the reaction medium during this controlled hydrolysis step. After filtration, enabling the enzymes and polymers to be eliminated, the filtrate (solution) obtained constitutes a first form of the active principle according to the invention.

The hydrolyzate obtained at this stage may be purified again in order to select the low molecular weight fractions, preferentially lower than 6 kDa, and the peptides generated according to their nature. Fractionation may be advantageously carried out by successive ultrafiltration steps through filters of decreasing porosity, by conserving the filtrates at each step and/or by a chromatographic type method, in order to specifically enrich the hydrolyzate in bioactive peptide.

The invention carries out a phase of dilution in water or in any mixture containing water, and then sterilization by ultrafiltration in order to obtain a peptidic hydrolyzate characterized by a protein content from 0.5 to 5.5 g/l. This peptidic hydrolyzate corresponds to the most purified form of the active principle according to the invention.

The peptidic hydrolyzate obtained according to the invention is qualitatively and quantitatively analyzed in high pressure liquid chromatography (HPLC), enabling the proteins having molecular weights from 0.2 to 25 kDa (according to a gradient of appropriate solvents) to be analyzed. The different peptidic fractions that could be isolated are then analyzed for their biological effectiveness. These diverse fractions are then analyzed by mass spectrometry in order to specifically identify the amino acid content of the peptides from each peak. A sequencing analysis was also carried out, to determine the peptidic sequence of the bioactive peptide.

The hydrolyzate obtained is composed of peptides with a molecular weight lower than 6 kDa, preferentially lower than 6 kDa, and enriched in bioactive peptide from 4 to 6 amino acids comprising at least one glycine residue, one leucine residue and one glutamic acid residue.

The second object of the present invention is a composition comprising, in a physiologically acceptable medium, the peptidic hydrolyzate enriched in bioactive peptide according to the invention as the active principle capable of reinforcing the barrier function of the epidermis.

According to an advantageous embodiment of the invention, the active principle according to the invention is present in the compositions of the invention at a concentration of between approximately 0.0001% and 20%, and preferentially at a concentration of between approximately 0.05% and 5% with relation to the total weight of the final composition.

According to an advantageous embodiment of the invention, the active principle according to the invention is solubilized in one or more physiologically acceptable solvents, conventionally used by the person skilled in the art, such as water, glycerol, ethanol, propylene glycol, butylene glycol, dipropylene glycol, ethoxylated or propoxylated diglycols, cyclic polyols, white petroleum jelly, vegetable oil or any mixture of these solvents.

According to another advantageous embodiment of the invention, the active principle according to the invention is previously solubilized in a cosmetic or pharmaceutical carrier such as liposomes, or adsorbed on powdery organic polymers, mineral supports such as talcs and bentonites, and more generally solubilized in, or fixed on, any physiologically acceptable carrier.

The usable composition according to the invention may in particular consist of a composition for capillary care, and particularly a shampoo, a conditioner, a treatment lotion, a hairdressing cream or gel, a restructuring lotion for the hair, a mask, etc. The composition may also be present in the form of hair tint or mascara to be applied by brush or comb, in particular onto the eyelashes, eyebrows or hair.

The usable composition according to the invention will be applied by any appropriate route, notably oral, parenteral or topical, and the formulation of the compositions will be adapted by the person skilled in the art, in particular for cosmetic or dermatological compositions. Advantageously, the compositions according to the invention are intended for topical administration. These compositions therefore must contain a physiologically acceptable medium, i.e., a medium compatible with the skin and epithelial appendages, and must cover all cosmetic or dermatological forms.

It is understood that the active principle according to the invention may be used alone or in combination with other active principles.

Advantageously, the usable compositions according to the invention may also contain various protective or antiaging active principles intended to promote and supplement the action of the active principle. In a non-limiting manner, the following ingredients may be cited: cicatrizant, anti-age, anti-wrinkle, smoothing, anti-radical, anti-UV agents, agents stimulating the synthesis of dermal macromolecules or energy metabolism, moisturizing, antibacterial, antifungal, anti-inflammatory, anesthetic agents, agents modulating cutaneous differentiation, pigmentation or depigmentation, agents stimulating nail or hair growth. Preferentially, an agent presenting anti-wrinkle activity, such as an anti-radical or antioxidant agent, or an agent stimulating the synthesis of dermal macromolecules, an agent stimulating energy metabolism, a metalloproteinase inhibitor will be used.

For example, other active principles having an anti-radical or antioxidant action, chosen from among vitamin C, vitamin E, coenzyme Q10, and polyphenolic plant extracts, retinoids, may be added.

The composition according to the invention may likewise associate with the active principle according to the invention other active principles stimulating the synthesis of dermal macromolecules (laminin, fibronectin, collagen), for example the collagen peptide sold under the name "Collaxyl®" by the Vincience company.

The composition according to the invention may also associate with the active principle according to the invention other active principles stimulating energy metabolism, such as the active principle sold under the name "GP4G®" by the Vincience company.

Of course, it is obvious that the invention is aimed at mammals in general, and more particularly at human beings.

These compositions may particularly be present in the form of an aqueous solution, hydroalcoholic or oily solution; an oil in water emulsion, water in oil emulsion or multiple emulsions; they may also be present in the form of creams, suspensions or else powders, suitable for application on the skin, mucosa, lips and/or epithelial appendages. These compositions may be more or less fluid and have the appearance of a cream, a lotion, a milk, a serum, a pomade, a gel, a paste or a foam. They may also be present in solid form, such as a stick, or may be applied on the skin in aerosol form. They may be used as a care product and/or as a skin makeup product.

All of these compositions also comprise any additive commonly used in the contemplated field of application as well as the adjuvants necessary for their formulation, such as solvents, thickeners, diluents, antioxidants, colorants, sunscreens, self-tanning agents, pigments, fillers, preservatives, fragrances, odor absorbers, other cosmetic active principles, essential oils, vitamins, essential fatty acids, surface active agents, film-forming polymers, etc.

In all cases, the person skilled in the art will make sure that these adjuvants as well as their proportions are chosen so as to not harm the desired advantageous properties of the composition according to the invention. These adjuvants may, for example, correspond to a concentration ranging from 0.01 to 20% of the total weight of the composition. When the composition of the invention is an emulsion, the fatty phase may represent from 5 to 80% by weight and preferably from 5 to 50% by weight with relation to the total weight of the composition. The emulsifiers and co-emulsifiers used in the composition will be chosen from among those conventionally used in the field under consideration. For example, they may be used in a proportion going from 0.3 to 30% by weight with relation to the total weight of the composition.

The third object of the invention is a pharmaceutical composition comprising an effective quantity of peptidic hydrolyzate according to the invention, as a drug. For example, the pharmaceutical composition may be intended to prevent or treat pathologies characterized by an alteration in the barrier function, such as hypersensitive, irritated or reactive skin and atopic eczema.

According to this form of the invention, the compositions will be suitable for oral administration for pharmaceutical use. Thus, the compositions may in particular be present in the form of tablets, capsules, gel capsules, chewable pastes, powders to consume as is or to be mixed immediately before use with a liquid, syrup, gels or any other form known to the person skilled in the art. These compositions also comprise any additive commonly used in the contemplated field of application as well as the adjuvants necessary for their formulation, such as solvents, thickeners, diluents, antioxidants, preservatives, other pharmaceutical active principles, essential oils, vitamins, essential fatty acids, etc.

The fourth object of the invention is the use, in a cosmetic composition, of an effective quantity of peptidic hydrolyzate, as an active principle that activates human HMG-CoA reductase.

The effective quantity of active principle corresponds to the quantity necessary for obtaining the desired result, that is, to activate HMG-CoA reductase, in the goal of improving the barrier function of the epidermis and stimulating epidermal differentiation.

"Strengthen the barrier function of the skin and stimulate epidermal differentiation" is understood to refer to the improvement in the protection capacity of the horny layer of the epidermis and the increase in the expression of biological differentiation markers, such as keratins.

Thus, thanks to the special properties of said active principle, it can be used in a cosmetic composition intended to strengthen the barrier function of the skin and to stimulate epidermal differentiation.

On the other hand, the peptidic hydrolyzate may be used advantageously as an active principle in a cosmetic composition intended to preventively and/or curatively combat the signs of cutaneous aging, and more particularly photo-induced cutaneous aging (photo aging). Cutaneous signs of aging or photo-aging is understood to refer to any modifications in the external appearance of the skin and epithelial appendages due to aging such as, for example, superficial roughness of the horny layer of the epidermis, wrinkles and fine lines, but also any internal modification of the skin that is not systematically manifested in a modified external appearance such as, for example, thinning of the epidermis or any other internal degradation of the skin following exposure to ultraviolet (UV) radiation.

According to another aspect of the invention, the peptidic hydrolyzate can be used advantageously as an active principle in a cosmetic composition intended to protect the skin against all types of external stresses.

The expression "external stress" is understood to refer to stresses that the environment may produce. By way of example one may cite stresses such as pollution, UV radiation or else irritating products such as surface active agents, preservatives or fragrances, or mechanical stresses, such as abrasions, shaving or epilation. Pollution is understood to refer to both "external" pollution, due for example to diesel particles, ozone or heavy metals and to "internal" pollution, that may be particularly due to the emissions from paint, adhesive or wallpaper solvents (such as toluene, styrene, xylene or benzaldehyde), or else to cigarette smoke. Dryness of the atmosphere is also an important cause of skin stress. These external stresses result in an alteration of the barrier function that results in skin discomfort, disagreeable sensory phenomena, such as tearing pain or itching and even excessive fragility and redness.

In particular, the object of the invention is the use of the hydrolyzate according to the invention in a cosmetic composition intended to prevent or treat damage caused to the skin by external stresses of the skin, chosen from among mechanical treatments such as shaving or epilation, overly intense washings by detergents, extreme climactic conditions or sudden variations in temperature and hygrometry.

The fifth object of the invention is a cosmetic treatment method intended to prevent and/or combat cutaneous signs of aging and/or photo-aging, according to which a composition comprising an effective quantity of peptidic hydrolyzate according to the invention is applied onto the areas to be treated.

Particular embodiments of this cosmetic treatment method also result from the previous description. Other advantages and characteristics of the invention will more clearly appear upon reading the examples given for illustrative and non-limiting purposes.

LIST OF FIGURES

FIG. 1: Chromatogram example obtained by HPLC, with demonstration of the peak corresponding to the bioactive peptide in a einkorn hydrolyzate;

FIG. 2: Chromatogram example obtained by HPLC, with demonstration of the peak corresponding to the bioactive peptide in a potato hydrolyzate;

FIG. 3: Chromatogram example obtained by HPLC, with demonstration of the peak corresponding to the bioactive peptide in a corn hydrolyzate;

FIG. 4: Chromatogram example obtained by HPLC, with demonstration of the peak corresponding to the bioactive peptide in a pea hydrolyzate;

FIG. 5: Chromatogram example obtained by HPLC, with demonstration of the peak corresponding to the bioactive peptide in a soy hydrolyzate.

FIG. 6: Chromatogram example obtained by HPLC, with demonstration of the peak corresponding to the bioactive peptide in a *Saccharomyces cerevisiae* hydrolyzate

EXAMPLE 1

Preparation of a Peptidic Hydrolyzate from Einkorn (*Triticum monococcum*)

Grains of einkorn (*Triticum monococcum*) were dissolved in 10 volumes of water in the presence of 2% of POLYCLAR® 10 (polyvinylpyrrolidone-PVPP—insoluble). The mixture was adjusted to a pH in the range 6 to 8 with an aqueous 1M solution of sodium hydroxide.

After adjusting the pH, an amylase (Hasidase®) and a protease (papain, 2%) were added to the reaction medium. Hydrolysis was complete after 2 hours mixing at 50° C. Next, the enzyme was inactivated by heating the solution to 80° C. for 2 hours. After centrifuging, the supernatant aqueous solution corresponding to a crude einkorn hydrolyzate was recovered. The hydrolysis conditions had been selected so as to allow an enrichment in bioactive peptide containing 4 to 6 amino acids containing the residues Gly, Leu and glutamic acid.

The method for the purification of the crude hydrolyzate commenced with successive filtrations using Seitz-Orion filter plates with decreasing porosity (to 0.2 µm) in order to obtain a bright, clear solution termed hydrolyzate 1.

In this step, the einkorn hydrolyzate 1 was characterized by a clear yellow colour and by a dry extract assaying at 20 to 25 g/kg, a protein content of 10 to 12 g/l and a sugar content of 5 to 8 g/l.

The protein nature of hydrolyzate 1 was identified after electrophoretic analysis on NuPAGE® Bis-Tris Pre-cast polyacrylamide gel (Invitrogen). The einkorn protein hydrolyzate was heated to 70° C. for 10 minutes under reducing denaturing conditions in a NuPAGE® LDS sample preparation buffer. A solution of NuPAGE® antioxidizing agent was added to the internal cell (cathode) to prevent the reduced proteins from re-oxidizing during electrophoresis. Protein migration was carried out in a NuPAGE® MES migration buffer with the standard SeeBlue Plus2 as a molecular weight marker. Protein staining was carried out using Coomassie Blue® R-250. Under these conditions, a band was observed at 24 kDa, corresponding to the enzyme, then smaller proteins at 6 kDa.

Hydrolyzate 1 was then purified by ultrafiltration using a Pellicon® 2 Biomax 5 kDa cassette in order to eliminate all traces of enzymes. At the end of purification, a yellow-orangey peptide hydrolyzate was obtained which was bright and clear. A dilution phase was carried out to obtain a peptide hydrolyzate characterized by a protein content of 1.5 to 3.5 g/l. This peptide hydrolyzate corresponded to the active principle of the invention.

This peptide hydrolyzate was then analyzed using high pressure liquid chromatography (HPLC) with the aid of a HP 1100 apparatus controlled using ChemStation software. The column used during elution of the hydrolyzate was a Nucleosil® 300-5 C4 MPN (125×4 mn) column which allowed proteins with molecular weights of 0.2 to 25 kDa to be chromatographed under the following conditions:

A Methanol gradient:

Uptisphere OPB 125×3 mm column

Solvent A: HPLC grade water containing 0.1% heptaflurobutyric acid (HFBA)

Solvent B: HPLC grade methanol

Gradient: 100% to 40% solvent A in 13 min and then 40% to 10% in 5 min

Under these chromatographic conditions, several peptidic fractions were isolated. An example of a chromatogram obtained by HPLC (high pressure liquid chromatography), identifying a peak corresponding to the bioactive peptide is given in FIG. 1.

These various fractions were then analyzed by mass spectrometry in order to specifically identify the amino acid content of the peptides of each peak. Sequencing analysis was also carried out in order to determine the peptide sequence of the bioactive peptide.

The amino acid composition of the active principle of the invention was also determined. It was carried out after acid hydrolysis and identification by high pressure liquid chromatography using PICT (phenylisothiocyanate) pre-column derivatization.

An example of the amino acid composition of the hydrolyzate is given in the following table (in %):

| Amino acids | % |
| --- | --- |
| Alanine | 3.1 |
| Aspartic Acid | 4.7 |
| Arginine | 3.1 |
| Glutamic Acid | 32.8 |
| Glycine | 3.1 |
| Histidine | <3.0 |
| Isoleucine | <5.5 |
| Leucine | 6.2 |
| Lysine | <2.2 |
| Phenylalanine | 4.5 |
| Proline | 10.9 |
| Serine | 4.7 |
| Threonine | 3.1 |
| Tyrosine | <3.6 |
| valine | 4.7 |
| Tryptophan | <1.5 |

EXAMPLE 2

Preparation of a Peptidic Hydrolyzate from Tubers Belonging to the *Solanum tuberosum* Species Potato tubers (*Solanum tuberosum*) are put in solution in 10 volumes of water in the presence of 2% POLYCLAR® 10 (polyvinylpyrrolidone—PVPP-insoluble). The mixture is adjusted to a pH of between 6 and 8 with an aqueous solution of sodium hydroxide 1 M. Precipitation in acidic medium is then carried out. The pellet is put back into solution and after adjustment of the pH, papain 2% is added to the reaction medium. The hydrolysis is obtained after 2 hours of agitation at 55° C. The enzyme is then inactivated by heating the solution to 80° C. for 2 hours. After centrifugation, the supernatant aqueous solution corresponding to a crude potato hydrolyzate is recovered. The hydrolysis conditions have been chosen so as to enable bioactive peptide enrichment of 4 to 6 amino acids containing Gly, Leu and Glu residues.

The crude hydrolyzate purification process starts by successive filtrations by using Seitz-Orion filter plates of decreasing porosity (up to 0.2 μm) in order to obtain a bright and clear yellow solution, described as hydrolyzate 1.

At this step, the potato hydrolyzate 1 is characterized by a dry extract titrating from 40 to 60 g/kg, a protein level from 20 to 25 g/l and a sugar level from 1 to 3 g/l.

The protein nature of hydrolyzate 1 is demonstrated after electrophoresis analysis on NuPAGE® Bis-Tris Pre-cast (Invitrogen) polyacrylamide gel. The potato protein hydrolyzate is heated to 70° C. for 10 minutes under reducing denaturing conditions in a NuPAGE® LDS sample preparation buffer. A NuPAGE® Antioxidant solution is added into the inner tank (cathode) to prevent the reduced proteins from reoxidizing during the electrophoresis. Protein migration is carried out in the NuPAGE® MES migration buffer with the standard See-Blue Plus2 as a molecular weight marker. Protein coloration is carried out by using Coomassie Blue® R-250. Under these conditions, it is observed that the proteins obtained have a molecular weight of less than 6 kDa.

The hydrolyzate 1 is then purified in order to only retain peptides with a molecular weight of less than 5 kDa by using tangential flow filtration. To do this, the hydrolyzate 1 is pumped under pressure through a Pellicon® support equipped with a Pellicon® 2 Biomax cassette 5 kDa. At the end of purification, a bright and clear peptidic hydrolyzate is obtained. A dilution phase is carried out in order to obtain a peptidic hydrolyzate characterized by a protein content from 3.5 to 5.5 g/l. This peptidic hydrolyzate corresponds to the active principle according to the invention.

This peptidic hydrolyzate is then analyzed by high pressure liquid chromatography (HPLC) by using an HP1100 apparatus run by the ChemStation software. The column used during elution of the hydrolyzate is a Nucleosil® 300-5 C4 MPN (125×4 mn), enabling the proteins having molecular weights from 0.2 to 25 kDa to be chromatographed (according to conditions identical to example 1). Under these chromatographic conditions, several peptidic fractions could be isolated.

These diverse fractions are then analyzed by mass spectrometry in order to specifically identify the amino acid content of the peptides from each peak. A sequencing analysis was also carried out, to determine the peptidic sequence of the bioactive peptide.

An example of a chromatogram obtained by HPLC (high pressure liquid chromatography), with demonstration of the peak corresponding to the bioactive peptide is given in FIG. 2.

The determination of the composition in amino acids of the active principle according to the invention was also carried out. This is achieved after acid hydrolysis and identification by high pressure liquid chromatography by using pre-derivation with PICT (phenylisothiocyanate).

An example of the amino acid composition of the hydrolyzate is given in the following table (in %):

| Amino acids | % |
| --- | --- |
| Alanine | 7.8 |
| Aspartic Acid | 20.1 |
| Arginine | 7.3 |
| Glutamic Acid | 17.4 |
| Glycine | 7.3 |
| Histidine | 3.2 |
| Isoleucine | 9.1 |
| Leucine | 15.1 |
| Lysine | 11.4 |
| Phenylalanine | 8.7 |
| Proline | 7.7 |
| Serine | 8.7 |
| Threonine | 9.1 |
| Tyrosine | 8.2 |
| valine | 10.5 |
| Tryptophan | 1.4 |

EXAMPLE 3

Preparation of a Peptidic Hydrolyzate from Corn Germ Cake (*Zea mays* L.)

The corn germ cake (*Zea mays* L.) is put in solution in 10 volumes of water in the presence of 2% POLYCLAR® 10 (polyvinylpyrrolidone—PVPP-insoluble). The mixture is adjusted to a pH of between 6 and 8 with an aqueous solution of sodium hydroxide 1 M.

After adjustment of the pH, papain at 2% is added to the reaction medium. The hydrolysis is obtained after 2 hours of agitation at 55° C. The enzyme is then inactivated by heating the solution to 80° C. for 2 hours. After centrifugation, the supernatant aqueous solution corresponding to a crude corn hydrolyzate is recovered. The hydrolysis conditions have been chosen so as to enable bioactive peptide enrichment of 4 to 6 amino acids containing Gly, Leu and Glu residues.

The crude hydrolyzate purification process starts by successive filtrations by using Seitz-Orion filter plates of decreasing porosity (up to 0.2 μm) in order to obtain a bright and clear yellow solution, described as hydrolyzate 1.

At this step, the corn hydrolyzate 1 is characterized by a dry extract titrating from 20 to 30 g/kg, a protein level from 20 to 25 g/l and a sugar level from 2 to 5 g/l.

The protein nature of hydrolyzate 1 is demonstrated after electrophoresis analysis on NuPAGE® Bis-Tris Pre-cast (Invitrogen) polyacrylamide gel. The corn protein hydrolyzate is heated to 70° C. for 10 minutes under reducing denaturing conditions in a NuPAGE® LDS sample preparation buffer. A NuPAGE® Antioxidant solution is added into the inner tank (cathode) to prevent the reduced proteins from reoxidizing during the electrophoresis. Protein migration is carried out in the NuPAGE® MES migration buffer with the standard See-Blue Plus2 as a molecular weight marker. Protein coloration is carried out by using Coomassie Blue® R-250. Under these conditions, proteins with a molecular weight of less than 6 kDa are observed.

The hydrolyzate 1 is then purified by eliminating high molecular weight proteins by ultrafiltration by using the Pellicon® 2 Biomax cassette 5 kDa in order to only retain peptidic nature compounds of less than 5 kDa.

After this final purification, a dilution phase is carried out in order to obtain a peptidic hydrolyzate characterized by a protein level of between 3.5 and 5.5 g/l. This peptidic hydrolyzate corresponds to the active principle according to the invention.

This peptidic hydrolyzate is then analyzed by high pressure liquid chromatography (HPLC) by using an HP1100 apparatus run by the ChemStation software. The column used during elution of the hydrolyzate is a Nucleosil® 300-5 C4 MPN (125×4 mn) column, enabling the proteins having molecular weights from 0.2 to 25 kDa to be chromatographed (according to a suitable solvent gradient, identical to example 1). Under these chromatographic conditions, several peptidic fractions could be isolated.

An example of a chromatogram obtained by HPLC (high pressure liquid chromatography), with demonstration of the peak corresponding to the bioactive peptide is given in FIG. 3.

These diverse fractions are then analyzed by mass spectrometry in order to specifically identify the amino acid content of the peptides from each peak. A sequencing analysis was also carried out, to determine the peptidic sequence of the bioactive peptide.

The determination of the composition in amino acids of the active principle according to the invention was also carried out. This is achieved after acid hydrolysis and identification by high pressure liquid chromatography by using pre-derivation with PICT (phenylisothiocyanate). An example of the amino acid composition of the hydrolyzate is given in the following table (%):

| Amino acids | % |
|---|---|
| Alanine | 9.4 |
| Aspartic Acid | 7.2 |
| Arginine | 3.6 |
| Glutamic Acid | 23.7 |
| Glycine | 3.6 |
| Histidine | 2.2 |
| Isoleucine | 4.5 |
| Leucine | 16.1 |
| Lysine | 2.2 |
| Phenylalanine | 6.7 |
| Proline | 10.3 |
| Serine | 6.3 |
| Threonine | 4.0 |
| Tyrosine | 5.8 |
| valine | 5.4 |
| Tryptophan | <0.5 |

EXAMPLE 4

Preparation of a Peptidic Hydrolyzate from Peas (*Pisum sativum* L.)

The peptidic hydrolyzate is obtained from a plant extract of the *Pisum sativum* L species. Of course, the extract may be prepared from plants of at least any one of the many varieties and species belonging to the *Pisum* genus.

In a first step, 1 kg of hulled peas are de-fatted by the action of an organic solvent: hexane.

The pea flour thus obtained is put in solution in 10 volumes of water in the presence of 2% POLYCLAR® 10 (polyvinylpyrrolidone—PVPP-insoluble). The mixture is adjusted to a pH of between 6 and 7 with an aqueous solution of sodium hydroxide 1 M.

After adjustment of the pH, Flavourzyme® at 2% is added to the reaction medium. Hydrolysis is obtained after 2 hours of agitation at 50° C. The enzyme is then inactivated by heating the solution to 80° C. for 2 hours. The reaction mixture thus obtained corresponds to the pea extract. The hydrolysis conditions have been chosen so as to enable bioactive peptide enrichment of 4 to 6 amino acids containing Gly, Leu and Glutamic acid residues.

The purification process starts by successive filtrations by using Seitz-Orion filter plates of decreasing porosity (up to 0.2 µm) in order to obtain a bright and clear solution. In this step, the pea hydrolyzate is characterized by a dry extract of 70-80 g/kg, a protein level of 55-65 g/l, a sugar level of 2-5 g/l and a polyphenol level of 1-3 g/l.

The protein nature of this hydrolyzate is demonstrated by electrophoresis on polyacrylamide gel. For this analysis, NuPAGE® Bis-Tris Pre-cast (Invitrogen) gels are used. The pea peptidic hydrolyzate is heated to 70° C. for 10 minutes under reducing denaturing conditions in a NuPAGE® LDS sample preparation buffer. A NuPAGE® Antioxidant solution is added into the inner tank (cathode) to prevent the reduced proteins from reoxidizing during electrophoresis. Protein migration is carried out by using the NuPAGE® MES migration buffer with the standard SeeBlue Plus2 as a molecular weight marker. Protein coloration is carried out by using Coomassie Blue® R-250. Under these conditions, 2 large protein families are observed: The $1^{st}$ family corresponds to proteins of molecular weight from 25 to 20 kDa and the last family to proteins of molecular weight of less than 5 kDa.

This solution is then purified by eliminating proteins of molecular weight greater than 5 kDa by using tangential flow filtration.

To do this, the pea hydrolyzate is pumped under pressure through a Pellicon® support equipped with a Pellicon® 2 Biomax cassette 30 kDa. This $1^{st}$ filtrate is recovered to then be filtered through another Pellicon® 2 Biomax cassette 5 kDa. At the end of purification, a bright and clear yellow-beige pea peptidic hydrolyzate is obtained. It is characterized by a dry extract of 50 to 55 g/kg, a protein content of 50 to 52 g/l.

This solution is then analyzed by high pressure liquid chromatography (HPLC) by using an HP1100 apparatus run by the ChemStation software. The column used during elution of the pea extract is a Nucleosil® 300-5 C4 MPN (125×4 mn) column. This column enables proteins having molecular weights of 0.2 to 25 kDa to be chromatographed (according to a suitable solvent gradient, identical to example 1). Under these chromatographic conditions, several peptidic fractions could be isolated.

These diverse fractions are then analyzed by mass spectrometry in order to specifically identify the amino acid content of the peptides from each peak. A sequencing analysis was also carried out, to determine the peptidic sequence of the bioactive peptide. An example of a chromatogram obtained by HPLC (high pressure liquid chromatography), with demonstration of the peak corresponding to the bioactive peptide is given in FIG. 4.

The determination of the composition in amino acids of the active principle according to the invention was also carried out. This is achieved after acid hydrolysis and identification by high pressure liquid chromatography by using pre-derivation with PICT (phenylisothiocyanate).

EXAMPLE 5

Preparation of a Peptidic Hydrolyzate from Soybean Cake (*Glycine max* . L.)

The active principle is obtained from plants from the *Glycine max* L species. Of course, the extract may be prepared from plants of at least any one of the many varieties and species belonging to the *Glycine* genus. The cakes are solid residues obtained after extracting the oil from soy beans. They represent from 50 to 75% of the bean mass.

In a first step, 1 kg of soybean cake is ground in a grain mill. The flour obtained is de-fatted by the action of an organic solvent, hexane. After filtration and vacuum drying, the powder obtained is suspended in an alkaline aqueous solution (1:10 dilution) pH 10, containing 1% polyvinylpolypyrrolidone (Polyclar V ISP). This mixture is maintained under agitation for a sufficiently long time to enable solubilization of the soluble fractions. The extraction temperature is variable (between 4 and 80° C.); preferentially, the operation will be carried out cold. After this extraction phase, the medium is clarified by centrifugation and then filtered on a plate filter. This filtrate that contains soluble soy fractions is then subjected to protein precipitation by varying the ionic strength in neutral or acidic medium, which enables soluble glucidic components, lipids and nucleic acids to be eliminated. The medium is brought to pH 3.5. The supernatant is eliminated and the precipitate is then washed by using a solvent such as, for example, ethanol or methanol, and then the solvent is evaporated by vacuum drying.

At this stage, approximately 50 grams of pale yellow crude protein extract powder are obtained containing:

Proteins: 75%
Carbohydrates: 20%
Lipids: 5%

The protein-rich precipitate is put back in solution in water or another solvent.

The crude protein extract is then subjected to a series of controlled and selective hydrolyses consisting of chemical and enzymatic hydrolyses in the presence of 0.5% PVPP (Polyclar V) and cysteine endopeptidases (papain, ficin). After reaction, the hydrolyzate is filtered on a plate and then on sterilizing cartridge (0.2 µm).

A pale hydrolyzate is then obtained, titrating from 15 to 30 g/l of dry extract, that is then diluted such that the concentration of peptidic nature compounds determined by the Lowry method is between 0.1 and 5 g/l and preferentially between 0.5 and 2 g/l. The physical chemical analysis of the peptidic hydrolyzate, that constitutes the active principle, shows that its pH is between 4 and 7, and preferentially between 5 and 6, the dry extract titers from 1 to 8 g/l and preferably from 2 to 5 g/l, its peptidic nature compound content is between 0.1 and 5 g/l, and preferentially between 0.5 and 2 g/l and its sugar content is between 0.5 to 2.5 g/l. The hydrolysis conditions have been chosen so as to enable bioactive peptide enrichment of 4 to 6 amino acids containing Gly, Leu and Glutamic acid residues.

The solution is then ultrafiltrated on a Millipore Helicon filtration cartridge (cutoff 1 kDa). The high molecular weights contained in the retentate are separated, the filtrate is retained.

This solution is then analyzed by high pressure liquid chromatography (HPLC) by using an HP1100 apparatus run by the ChemStation software. The column used during elution of the soy hydrolyzate is a Nucleosil® 300-5 C4 MPN (125×4 mn) column. This column enables proteins having molecular weights of 0.2 to 25 kDa to be chromatographed (according to a suitable solvent gradient, identical to example 1). Under these chromatographic conditions, several peptidic fractions were isolated.

These diverse fractions are then analyzed by mass spectrometry in order to specifically identify the amino acid content of the peptides from each peak. A sequencing analysis was also carried out, to determine the peptidic sequence of the bioactive peptide. An example of a chromatogram obtained by HPLC (high pressure liquid chromatography), with demonstration of the peak corresponding to the bioactive peptide is given in FIG. 5.

The determination of the composition in amino acids of the active principle according to the invention was also carried out. This is achieved after acid hydrolysis and identification by high pressure liquid chromatography by using pre-derivation with PICT (phenylisothiocyanate).

A variation of the protocol consists of purifying the active principle, obtained according to the previous protocol, by ion exchange chromatography, on a TSK gel column (TosoHaas) with a pH 7 phosphate buffer, in order to enrich the peptidic hydrolyzate in bioactive peptide.

EXAMPLE 6

Preparation of a Peptidic Hydrolyzate from *Saccharomyces Cerevisiae* Yeasts

The peptidic hydrolyzate may be obtained from an extract of yeasts from the *Saccharomyces cerevisiae* species. The yeasts are cultivated in a suitable medium for their development, preferably in the presence of lactose, and then centrifuged to recover a biomass. The *saccharomyces* biomass is put in solution in 10 volumes of water in the presence of 2% POLYCLAR® 10 (polyvinylpyrrolidone—PVPP-insoluble) and 0.2% activated carbon. The mixture is adjusted to a pH of between 6 and 7.5 with an aqueous solution of sodium hydroxide 1 M.

After adjustment of the pH, 2% papain is added to the reaction medium. Hydrolysis is obtained after 2 hours of agitation at 55° C. The enzyme is then inactivated by heating the solution to 80° C. for 2 hours. After centrifugation, the reaction mixture corresponding to the *saccharomyces* extract is then obtained. The hydrolysis conditions have been chosen so as to enable bioactive peptide enrichment of 4 to 6 amino acids containing Gly, Leu and Glutamic acid residues.

The purification process starts by successive filtrations by using Seitz-Orion filter plates of decreasing porosity (up to 0.2 µm) in order to obtain a bright and clear solution. At this step, the *Saccharomyces* extract is characterized by a dry extract from 25 to 35 g/kg, a protein level from 10 to 15 g/l and a sugar level from 5-10 g/l.

The protein nature of this extract is demonstrated by electrophoresis on polyacrylamide gel. For this analysis, NuPAGE® Bis-Tris Pre-cast (Invitrogen) gels are used. The peptidic hydrolyzate is heated to 70° C. for 10 minutes under reducing denaturing conditions in a NuPAGE® LDS sample preparation buffer. A NuPAGE® Antioxidant solution is added into the inner tank (cathode) to prevent the reduced proteins from reoxidizing during electrophoresis. Protein migration is carried out by using the NuPAGE® MES migration buffer with the standard SeeBlue Plus2 as a molecular weight marker. Protein coloration is carried out by using Coomassie Blue® R-250. Under these conditions, 3 large protein families are observed: The $1^{st}$ family corresponds to proteins of molecular weight greater than 75 kDa, the $2^{nd}$ family to proteins from 20 to 25 kDa and the last family to proteins of molecular weight less than 5 kDa.

This solution is then purified by eliminating proteins of molecular weight greater than 5 kDa by using tangential flow filtration.

To do this, the *saccharomyces* peptidic hydrolyzate is pumped under pressure through a Pellicon® support equipped with a Pellicon® 2 Biomax cassette 50 kDa. This 1st filtrate is recovered to then be filtered through a second Pellicon® 2 Biomax cassette 10 kDa. A second filtrate is then recovered that is again eluted through a last Pellicon® 2 Biomax cassette 5 kDa. At the end of purification, a beige, bright and clear *saccharomyces* plant extract is obtained. It is characterized by a dry extract from 35 to 45 g/kg, a protein content from 30 to 40 g/l.

This solution is then analyzed by high pressure liquid chromatography (HPLC) by using an HP1100 apparatus run by the ChemStation software. The column used during elution of the *saccharomyces* hydrolyzate is a Nucleosil® 300-5 C4 MPN (125×4 mn) column. This column enables proteins having molecular weights of 0.2 to 25 kDa to be chromatographed (according to a suitable solvent gradient, identical to example 1). Under these chromatographic conditions, several peptidic fractions were isolated.

These diverse fractions are then analyzed by mass spectrometry in order to specifically identify the amino acid content of the peptides from each peak. A sequencing analysis was also carried out, to determine the peptidic sequence of the bioactive peptide.

The determination of the composition in amino acids of the active principle according to the invention was also carried out. This is achieved after acid hydrolysis and identification by high pressure liquid chromatography by using pre-derivation with PICT (phenylisothiocyanate).

EXAMPLE 7

Ultrastructural Study of Lamellar Bodies in Human Keratinocytes Treated by the Hydrolyzate According to Example 1

The goal of this study is to study in an ultrastructural manner, in transmission electron microscopy, keratinocytes treated by the hydrolyzate according to example 1 at 1%.
Protocol:
Normal human keratinocytes in culture are treated with a 1% hydrolyzate solution according to example 1 for 48 hours (the medium in the presence of the active principle is changed every 24 hours). The cells are washed in PBS, and then are fixed by Karnosky hypertonic fixation (4% paraformaldehyde, 5% glutaraldehyde in a 0.08 M phosphate buffer) 1 hour at ambient temperature and then 24 hours at 4° C. The cells are detached from the support by scraping and centrifuged 5 minutes at 1000 rpm. The supernatant is eliminated and a 1M sodium cacodylate buffer is deposited on the residue. The cells are mixed with 2% agar and then postfixed by osmium tetraoxide for 1 hour. The specimens are then dehydrated by successive passages in a series of alcohol (from 50 to 100%). The cells are then coated in a resin. The polymerization is carried out for approximately 12 hours at 60° C. Semi-thin sections of 0.5 µm are made with an ultramicrotome. The sections are deposited on a heat bonded slide and then colored with toluidine blue. The slides are then dehydrated again and mounted in a suitable medium. After having chosen the optimal study zone, the block is recut to the desired size and ultrathin sections are then made, only sections with a silver-grey color and a suitable size are mounted on the electron microscopy grid labeled with both uranyl acetate and lead citrate, and are examined by transmission electron microscope at 60 or 80 KV.
Results:
The ultrastructural study shows that the Golgi complex is substantially more developed than in the control cells. This increase is connected to an excess production of lamellar bodies (or Odland bodies) that is the sign of an increase in lipid synthesis.
Conclusions:
The hydrolyzate according to example 1 at 1% is capable of inducing an increase in lipid synthesis in normal human keratinocytes.

EXAMPLE 8

Ultrastructural Study of "Caveolae" in Human Fibroblasts Treated by the Hydrolyzate According to Example 2

The goal of this study is to study at the ultrastructural level the caveolae in human dermal fibroblasts.
Protocol:
Normal human dermal fibroblasts in culture are treated with the hydrolyzate according to example 2 at 1% for 48 hours (the medium containing the active principle is changed every 24 hours).
Results:
The ultrastructural study shows a significant increase in caveolae in cells treated by the hydrolyzate according to example 2 at 1%, in comparison with untreated control cells. These results are the sign of a positive effect of the active principle, since the caveolae are invaginations of the plasma membrane that enable the externalization of molecules such as cholesterol.
Conclusion:
The hydrolyzate according to example 2 at 1% causes the increase in membrane structures with externalization of cholesterol.

EXAMPLE 9

Differentiation Study of Human Keratinocytes Treated by the Hydrolyzate According to Example 2

The goal of this study is to determine the influence of the hydrolyzate according to the example on epidermal differentiation, and more particularly on the expression of all cytokeratins (or pankeratins), which are keratinocyte differentiation markers.
Protocol:
Normal human keratinocytes in culture are treated with the hydrolyzate according to example 2 at 1% for 48 hours (the medium in the presence of the active principle is changed every 24 hours). The cells are then washed and fixed with cold methanol for 4 minutes at 4° C. The cells are incubated in the presence of a monoclonal anti-cytopankeratin antibody at 1:200 for 1 hour at ambient temperature and are then revealed by a second antibody at 1:50 for 1 hour at ambient temperature, coupled with a fluorescent dye, "Alexa 488." After mounting in a ad hoc medium, the slides are observed by epifluorescence microscope.
Results:
The hydrolyzate according to example 2 increases the expression of pankeratins in the treated cells.
Conclusion:
The hydrolyzate according to example 2 at 1% increases the expression of cytokeratins in normal human keratinocytes. In the presence of the hydrolyzate according to example 2, the cells are stimulated and in pathway of differentiation.

EXAMPLE 10

Study of the Protective Effect of the Hydrolyzate According to Example 2 on Skin Cells Subjected to Ultraviolet Radiation (UVB)

The goal of this study is to determine the protective effect of the hydrolyzate according to example 2 with relation to normal human keratinocytes subjected to stress by UVB radiation. To do this, cellular viability tests were conducted by the MTT technique.
Protocol:
Normal human keratinocytes are treated with the hydrolyzate according to example 2 at 0.5% for 24 hours, irradiated by UVB (50 mJ/cm$^2$) and then cultivated again 24 hours in the presence of the same concentration of hydrolyzate according to example 2. Untreated and non-irradiated controls are carried out under the same conditions. At the end of the experiment, the cells are incubated in a solution containing 0.1 mg/ml of MTT (3-[4,5-dimethylthiazol-2-yl]-2,5-diphenyltetrazolium bromide). This compound is absorbed by the living cells and then metabolized by mitochondrial enzymes into a blue violet compound, formazan, that will be assayed by spectrophotometry at 540 nm. The optical density (O.D.) is then directly proportional to the mitochondrial enzymatic activity as well as to the number of living cells.

Results:

Evaluation of cellular viability by the MTT technique shows that the hydrolyzate according to example 2 increases cellular viability after UVB irradiation by 16%.

Conclusion:

The hydrolyzate according to example 2 at 0.5% increases cellular viability and effectively protects the skin cells from the cytotoxic effects of UVB radiation.

EXAMPLE 11

Study of the Expression of HMG-CoA Reductase in Skin Biopsies in the Presence of the Hydrolyzate According to Example 1

The goal of this study is to determine the influence of the hydrolyzate according to example 1 at 0.5% on the expression of HMG-CoA reductase.

Protocol:

Samples of human skin are placed in culture at the air/liquid interface. The hydrolyzate according to example 1 at 0.5% is applied topically, and then the samples are incubated for 24 hours or 48 hours.

These skin samples are then fixed with formaldehyde and then enclosed in paraffin. Sections of 2 to 3 μm are then made. Immunolabelling is carried out after unmasking the specific sites by microwave treatment and then incubation in trypsin. Immunolabelling is carried out by using a polyclonal rabbit antibody specific for HMG-CoA reductase (Millipore, Upstate), and then a secondary antibody, coupled with a fluorescent dye. The skin sections are then examined by epifluorescence microscope (Nikon Eclipse E600 microscope).

Results:

Microscopic observations show stronger fluorescence in skin treated by the hydrolyzate according to example 1 at 0.5%, in the upper layers of the epidermis, with relation to the untreated control.

Conclusion:

The hydrolyzate according to example 1 stimulates the expression of HMG-CoA reductase, in the upper layers of the epidermis.

EXAMPLE 12

Study of the Expression of HMG-CoA Reductase in Normal Human Keratinocytes in the Presence of the Hydrolyzate According to Example 2

The goal of this study is to determine the influence of the hydrolyzate according to example 2 on the expression of HMG-CoA reductase in normal human keratinocytes.

Protocol:

Normal human keratinocytes in culture are treated with the hydrolyzate according to example 2 at 0.5% for 24 or 48 hours (the medium containing the active principle is changed every 24 hours). The cells are then washed and fixed in cold methanol for 4 minutes at 4° C. The cells are incubated in the presence of a polyclonal rabbit antibody specific for HMG-CoA reductase (Millipore, Upstate), and then a secondary antibody coupled with a fluorescent dye. The cells are then examined by epifluorescence microscope (Nikon Eclipse E600 microscope).

Results:

Microscopic observations show more intense cytoplasmic fluorescence in cells treated by the hydrolyzate according to example 2 at 0.5%.

Conclusion:

The hydrolyzate according to example 2 at 0.5% stimulates the expression of HMG-CoA reductase in normal human keratinocytes.

EXAMPLE 13

Preparation of Compositions

1—Sun Protection Cream:

| Trade names | INCI names | Weight percent |
|---|---|---|
| PHASE A | | |
| Demineralized water | Aqua (Water) | qsp |
| Pemulen TR1 | Acrylates/C10-30 Alkyl Acrylate Crosspolymer | 0.40 |
| Glycerin | Glycerin | 3.00 |
| Nipastat Sodium | Sodium Methylparaben (and) Sodium Ethylparaben (and) Sodium Butyl paraben (and) Sodium Propylparaben (and) Sodium Isobutylparaben | 0.15 |
| PHASE B | | |
| Parsol MCX | Ethylhexyl Methoxycinnamate | 7.50 |
| Eusolex 4360 | Benzophenone-3 | 3.00 |
| Parsol 1789 | Butyl Methoxydibenzoyl-methane | 2.00 |
| Myritol 318 | Caprylic/Capric Triglyceride | 4.00 |
| Emulgade SEV | Hydrogenated Palm Glycerides (and) Ceteareth-20 (and) Ceteareth-12 (and) Cetearyl Alcohol | 5.00 |
| Propylparaben | Propylparaben | 0.15 |
| Nacol 16-98 | Cetyl Alcohol | 1.00 |
| PHASE C | | |
| TEA | Triethanolamine | 0.20 |
| PHASE D | | |
| Hydrolyzate according to example 1 | | 0.5% |
| Fragrance | Fragrance | qsp |
| Colorant | | qsp |

The constituents of phase A and phase B are heated separately between 70° C. and 75° C. Phase B is emulsified in phase A under stirring. Phase C is added at 45° C., by increasing the stirring. Phase D is then added when the temperature is below 40° C. The cooling is continued until 25° C. under intensive stirring.

2—Anti-Age Cream:

| Trade names | INCI names | Weight percent |
|---|---|---|
| Phase A | | |
| Montanov 68 | Cetearyl Alcohol (and) Cetearyl Glucoside | 6.00 |
| Squalane | Squalane | 3.00 |
| Cetiol SB 45 | *Butyrospermum Parkii* (Shea Butter) | 2.00 |
| Waglinol 250 | Cetearyl Ethylhexanoate | 3.00 |
| Amerchol L-101 | Mineral Oil (and) Lanolin Alcohol | 2.00 |
| Abil 350 | Dimethicone | 1.50 |
| BHT | BHT | 0.01 |
| Coenzyme Q10 | Ubiquinone | 0.10 |
| Phase B | | |
| Avocado Oil | *Persea Gratissima* (Avocado) Oil | 1.25 |
| Phenonip | Phenoxyethanol (and) Methylparaben (and) Ethylparaben (and) Butylparaben (and) Propylparaben (and) Isobutylparaben | 0.75 |
| Phase C | | |
| Demineralized water | Aqua (Water) | qsp |
| Butylene Glycol | Butylene Glycol | 2.00 |
| Glucam E10 | Methyl Gluceth-10 | 1.00 |
| Allantoin | Allantoin | 0.15 |
| Carbopol Ultrez 10 | Carbomer | 0.20 |
| Phase D | | |
| TEA | Triethanolamine | 0.18 |
| Phase E | | |
| Hydrolyzate according to example 1 | | 1% |
| GP4G | Water (and) *Artemia* Extract | 1.50 |
| Collaxyl | Water (and) Butylene Glycol (and) Hexapeptide-9 | 3.00 |
| Phase F | | |
| Fragrance | Fragrance | qsp |
| Colorant | | qsp |

Prepare and melt phase A at 65-70° C. Heat phase C to 65-70° C. Phase B is added to phase A just before emulsifying A into B. At approximately 45° C., the carbomer is neutralized by adding phase D. Phase E is then added under mild stirring and cooling is continued until 25° C. Phase F is then added if desired.

3—Protective Day Cream:

| Trade names | INCI names | Weight percent |
|---|---|---|
| Phase A | | |
| Emulium Delta | Cetyl alcohol (and) Glyceryl Stearate (and) PEG-75 Stearate (and) Ceteth-20 (and) Steareth-20 | 4.00 |
| Lanette O | Cetearyl Alcohol | 1.50 |
| D C 200 Fluid/100 cs | Dimethicone | 1.00 |
| DUB 810C | Coco Caprylate/Caprate | 1.00 |
| DPPG | Propylene Glycol Dipelargonate | 3.00 |
| DUB DPHCC | Dipentaerythrityl Hexacaprylate/Hexacaprate | 1.50 |
| Cegesoft PS6 | Vegetable Oil | 1.00 |
| Vitamin E | Tocopherol | 0.30 |
| Phenonip | Phenoxyethanol (and) Methylparaben (and) Ethylparaben (and) Butylparaben (and) Propylparaben (and) Isobutylparaben | 0.70 |
| Phase B | | |
| Demineralized water | Aqua | qsp 100 |
| Glycerin | Glycerin | 2.00 |
| Carbopol EDT 2020 | Acrylates/C10-30Alkyl Acrylate Crosspolymer | 0.15 |
| Keltrol BT | Xanthan Gum | 0.30 |
| Phase C | | |
| Sodium Hydroxide (10% sol.) | Sodium Hydroxide | 0.30 |
| Phase D | | |
| Demineralized water | Aqua | 5.00 |
| Stay-C 50 | Sodium Ascorbyl Phosphate | 0.50 |
| Phase E | | |
| Butylene Glycol | Butylene Glycol | 2.00 |
| Dekaben CP | Chlorphenesin | 0.20 |
| Phase F | | |
| GP4G | Water (and) *Artemia* Extract | 1.00 |
| Hydrolyzate according to example 1 | | 2% |

Prepare phase A and heat to 75° C. under stirring. Prepare phase B by dispersing the carbopol and then the xanthan gum under stirring. Let rest. Heat to 75° C.

At temperature, emulsify A into B under rotor stator stirring. Neutralize with phase C under rapid stirring. After cooling to 40° C., add phase D, and then phase E. Cooling is continued under mild stirring and phase F is added.

Applicants incorporate by reference the material contained in the accompanying computer readable Sequence Listing entitled "US09-122_collaxyl_ST25", which was created on Nov. 22, 2013, and is 2,701 bytes in size, and hereby confirm that the information recorded in the computer readable form is identical to the written sequence listing.

The invention claimed is:

1. A peptidic hydrolyzate comprising: one or more bioactive peptide each with a molecular weight of less than 6 kDa, each bioactive peptide or combination thereof reinforcing the barrier function of the epidermis, said bioactive peptide comprising 4 to 6 amino acids comprising at least one glycine residue, one leucine residue, and one glutamic acid residue, wherein said peptidic hydrolyzate is isolated from the hydrolysis of plants selected from the group consisting of einkorn (*Triticum monococum*), potato (*Solanum tuberosum*), corn (*Zea mayz* L.), pea (*Pisum sativum*) or from the hydrolysis of yeasts of the *Saccharomyces* genus.

2. The peptidic hydrolyzate according to claim 1, wherein said bioactive peptide is of general formula (I)

$$X_1\text{-[Gly,Glu,Leu]-}X_2\text{-}X_3$$

in which, $X_1$ is alanine, valine, isoleucine or absent, $X_2$ is serine or threonine, $X_3$ is leucine, isoleucine or absent.

3. The peptidic hydrolyzate according to claim 2, wherein said bioactive peptide is one of the following sequences:

Ala-Glu-Gly-Leu-Ser-Ile, (SEQ ID NO: 1)

Leu-Gly-Glu-Ser-Leu, (SEQ ID NO: 2)

Val-Gly-Glu-Leu-Thr, (SEQ ID NO: 3)

Ile-Gly-Glu-Leu-Ser, (SEQ ID NO: 4)

Ala-Gly-Glu-Leu-Ser, (SEQ ID NO: 5)

Gly-Glu-Leu-Thr-Ile, (SEQ ID NO: 6)

and

Gly-Glu-Leu-Ser. (SEQ ID NO: 7)

4. The peptidic hydrolyzate according to claim 1, wherein said peptidic hydrolyzate contains between 0.5 and 5.5 g/l of the bioactive peptide.

5. A cosmetic composition comprising:
   a physiologically acceptable medium; and
   a peptidic hydrolyzate in said medium, the peptide hydrolyzate comprising one or more bioactive peptide each with a molecular weight of less than 6 kDa, each bioactive peptide or combination thereof reinforcing the barrier function of the epidermis, said bioactive peptide comprising 4 to 6 amino acids comprising at least one glycine residue, one leucine residue, and one glutamic acid residue, said peptidic hydrolyzate is isolated from the hydrolysis of plants selected from the group consisting of einkorn (*Triticum monococum*), potato (*Solanum tuberosum*), corn (*Zea mayz* L.), pea (*Pisum sativum*) or from the hydrolysis of yeasts of the *Saccharomyces* genus; wherein the peptidic hydrolyzate is present in a quantity representing from 0.0001% to 20% of the total weight of the composition.

6. The composition according to claim 5, wherein said peptidic hydrolyzate is solubilized in one or more physiologically acceptable solvents selected from the group consisting of water, glycerol, ethanol, propylene glycol, butylene glycol, dipropylene glycol, ethoxylated or propoxylated diglycols, cyclic polyols, white petroleum jelly, vegetable oil, and combinations thereof.

7. The composition according to claim 5, wherein the composition is present in a form suitable for topical application.

8. The composition according to claim 5, wherein the composition further comprises at least one other active principle agent promoting the action of said peptidic hydrolyzate selected from the group consisting of vitamin C, vitamin E, coenzyme Q10, polyphenolic plant extracts, retinoids, the peptide of sequence Gly-Pro-Gln-Gly-Pro-Gln (SEQ ID NO: 8), the *Artemia* extract, and combinations thereof.

9. A cosmetic composition comprising:
   an effective quantity of a peptidic hydrolyzate as an active principle activating 3-hydroxy-3-methylglutaryl-Coenzyme A (HMG-CoA) reductase, said peptidic hydrolyzate comprising a bioactive peptide reinforcing the barrier function of the epidermis, said bioactive peptide containing 4 to 6 amino acids including at least one glycine residue, one leucine residue, and one glutamic acid residue.

10. A method for treating the cutaneous manifestations of aging and/or photo-aging, the method comprising:
    providing a composition comprising an effective quantity of a peptidic hydrolyzate, said peptidic hydrolyzate comprising one or more bioactive peptide each with a molecular weight of less than 6 kDa, each bioactive peptide or combination thereof reinforcing the barrier function of the epidermis, said bioactive peptide comprising 4 to 6 amino acids comprising at least one glycine residue, one leucine residue, and one glutamic acid residue wherein said peptidic hydrolyzate is isolated from the hydrolysis of plants selected from the group consisting of einkorn (*Triticum monococum*), potato (*Solanum tuberosum*), corn (*Zea mayz* L.), pea (*Pisum sativum*) or from the hydrolysis of yeasts of the *Saccharomyces* genus; and
    topically applying the composition to the skin or epithelial appendages to be treated.

11. The peptidic hydrolyzate according to claim 1, wherein the hydrolysis of yeasts is of the *Saccharomyces cerevisiae* species.

12. The cosmetic composition of claim 5, wherein the peptidic hydrolyzate is present in a quantity representing from 0.05% to 5% of the total weight of the composition.

13. A method for reinforcing the barrier function of the epidermis, the method comprising:
    providing a composition comprising a peptidic hydrolyzate isolated from the hydrolysis of plants selected from the group consisting of einkorn (*Triticum monococum*), potato (*Solanum tuberosum*), corn (*Zea mayz* L.), pea (*Pisum sativum*), soy (*Glycine Max.* L.), or yeast (*Saccharomyces cerevisiae*), said peptidic hydrolyzate comprising one or more bioactive peptide each with a molecular weight of less than 6 kDa, each bioactive peptide or combination thereof comprising 4 to 6 amino acids comprising at least one glycine residue, one leucine residue, and one glutamic acid residue; as an active principle activating HMG-CoA reductase; and
    topically applying the composition to the skin or epithelial appendages to be treated.

14. The method of claim 10, wherein topically applying includes the application of the cosmetic composition to the skin before exposure to an external stress.

15. The method of claim 14, wherein the external stress is selected from the group consisting of ultraviolet (UV) radiation, dryness of the atmosphere, or mechanical stresses chosen from abrasions, shaving, epilation, and combinations thereof.

16. The method of claim 10, wherein topically applying includes the application of the cosmetic composition to the skin after exposure to an external stress.

17. The method of claim 16, wherein the external stress is selected from the group consisting of ultraviolet (UV) radiation, dryness of the atmosphere, or mechanical stresses chosen from abrasions, shaving, epilation, and combinations thereof.

18. The method according to claim 13, wherein reinforcing the barrier function of the epidermis includes stimulating epidermal differentiation.

\* \* \* \* \*